United States Patent [19]

Kabbara

[11] Patent Number: 5,282,815
[45] Date of Patent: Feb. 1, 1994

[54] METHOD OF AND APPARATUS FOR PERFORMING SURGICAL INCISIONS

[76] Inventor: Jamil Kabbara, 29 Avenue Franklin Roosevelt, 75008 Paris, France

[21] Appl. No.: 908,215

[22] Filed: Jul. 2, 1992

[51] Int. Cl.$^5$ .............................................. A61B 17/32
[52] U.S. Cl. ..................................... 606/166; 128/898
[58] Field of Search ............... 606/166, 161, 172, 180; 128/898

[56] References Cited

U.S. PATENT DOCUMENTS

| | | | |
|---|---|---|---|
| 4,205,682 | 6/1980 | Crock et al. | 606/166 |
| 4,796,623 | 1/1989 | Krasner et al. | 606/166 |

*Primary Examiner*—Jerome L. Kruter
*Attorney, Agent, or Firm*—Rines and Rines

[57] ABSTRACT

An apparatus and method for performing an incision in, for example, the wall of the eye, including a suction cup which may be fixed to the wall of the eye, a cutting tool the cutting edge of which is in the shape of a closed curve, in particular a circle, surrounding tightly the rim of the suction cup, and capable of moving along the rim of the suction cup in order to penetrate into the wall of the eye and to incise it along the closed curve, means to create suction in the central zone of the suction cup in order to fix it firmly to the wall of the eye, and means to move the cutting tool along the rim of the suction cup, and to have it penetrate into the wall, at a depth at least equal to the thickness of the wall.

13 Claims, 1 Drawing Sheet

METHOD OF AND APPARATUS FOR PERFORMING SURGICAL INCISIONS

The present invention relates to methods of and apparatus for performing surgical incisions and the like, being more particularly directed to devices for performing an incision in the inner capsule of the crystalline lens of the eye and similar surgical applications.

BACKGROUND OF THE INVENTION

The subject matter of this invention is concerned with apparatus for performing an incision in the inner wall of the capsule for the removal of the crystalline lens of the eye during cataract surgery and the like, the art being replete with conventional techniques for achieving such ends.

While applicable, also, to other surgical and related applications, the invention is concerned more specifically with insuring immobilization of the surface to be incised, such as the wall of the eye, while the incision is made, and to the further insuring of the accuracy and control of the position of the line(s) of cut and the cleanness of such cut —features not heretofore totally satisfactorily addressed by prior surgical procedures.

In the important illustrative application to cataract surgery, where the apparatus serves the purpose of a so-called microcystotome, these results are admirably achieved, according to the invention, by a device that includes: (a) a suction cup which can be fixed on the wall of the crystalline lens; (b) a cutting tool with cutting edge or cutting path having the shape of a closed curve, in particular a circle, which surrounds tightly the rim of the suction cup and which can be moved along the rim of the suction cup in order to penetrate into the wall of the eye and to incise it along this closed curve (c) means to create suction in the central zone of the suction cup in order to fix it firmly on the wall of the eye; and (d) means to move the cutting tool along the rim of the suction cup in order to have it penetrate into the wall of the eye to a depth at least equal to the thickness of this wall.

It is through this technique, that the cutting tool can penetrate perpendicularly into the wall surface in the immediate proximity of the rim of the suction cup, which serves admirably to immobilize this wall, thus ensuring a very clean cut.

OBJECTS OF THE INVENTION

An object of the present invention, accordingly, is to provide a new and improved method of and apparatus or device for performing surgical incisions wherein the surface wall to be cut is held immobilized and the cut is effected with control along a predetermined curve with very clean incisions.

A further object is to provide a novel apparatus for performing such surgical incisions, particularly, though not exclusively, adapted for cutting and removing the crystalline lens of the eye during cataract surgery and the like.

Still an additional object is to provide a novel surgical incision apparatus of more general use, also, wherever the improved results of the invention are desired.

Other and further objects will be described hereinafter and are more particularly delineated in the appended claims.

SUMMARY OF INVENTION

In summary, from one of its important aspects, the invention embraces a method of surgical incision along a closed curve, such as a circle, of a surface to be cut, so as to remove the portion thereof within said closed curve, such as the inner circular disc portion of the crystalline lens of the eye, said method comprising, suction-attaching a cup to the said surface with said portion thereof lying within the opening of the cup and with the surface-attached cup rim defining said curve; disposing a cutting blade held a slight distance external to said cup rim by a holder positioned against the outer wall of the cup above the said cup rim; depressing the holder along said outer wall to insert the cutting blade into said surface; and moving the holder and cutting blade along the cup rim to incise the periphery of said portion of the surface within the said cup rim; and removing the cup and attached and incised surface portion as a unit, during the continued suction. Preferred and best mode designs and device or apparatus embodiments are later presented.

DRAWINGS

The invention will now be described more precisely with reference to the accompanying drawings, showing application to the illustrative non-limiting abovedescribed important ophthalmic surgical operations, and in which FIG. 1 is a longitudinal half-axial section of a preferred embodiment of the apparatus for practicing the technique of the invention, shown before the beginning of the incision; and FIG. 2 is a similar view at the end of the incision.

Proportions have not been respected on these diagrams for purposes of clarity.

DESCRIPTION OF PREFERRED EMBODIMENT OF THE INVENTION

Figure 1:
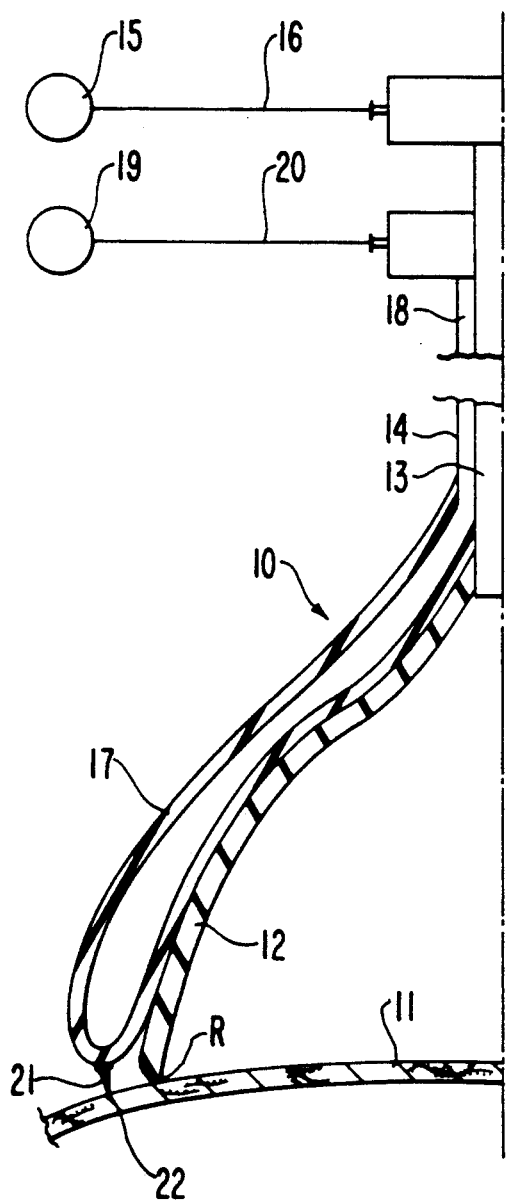
Figure 2:
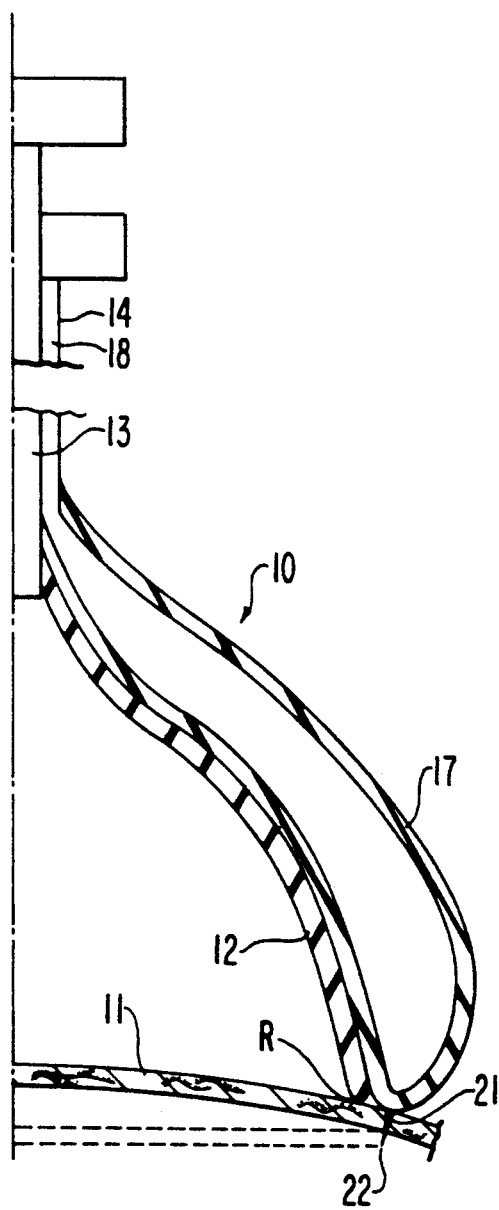

Referring to FIGS. 1 and 2, the surgical apparatus of the invention is generally designated at 10 and is shown resting on the wall surface 11 of the crystalline lens of the eye.

A somewhat conical, inverted suction cup 12, made of a rigid or semi-rigid material, as of rubber or the like, is applied to the wall surface 11. It is shown mounted on the end of the inner lumen 13 of a concentric double-lumen needle 14. This inner lumen 13 is connected at its opposite end to communicate with a source of suction 15 by a conduit 16 for providing suction within the cup 12. Suction applied at 15 will rapidly attach the suction cup rim R along its circular or closed curve periphery to the underlying ring of the wall surface 11, immobilizing the same and in particular the central portion lying within the opening of the cup inside the rim R.

A deformable somewhat conical enclosure 17 surrounds the outer wall of the suction cup 12 and is also attached to the needle 14, with the inner space of the enclosure pocket 17 connected, through the exterior lumen 18 of the needle 14 to a source of pressure 19, by a conduit 20. In FIG. 1, the enclosure 17 is deflated; and in FIG. 2 it has become pressure inflated for a reason now to be explained.

The lower rim of the deformable enclosure 17 is disposed near but outside the rim R of the inverted suction cup 12, and it carries preferably a ring-shaped cutting tool or blade 21. The blade 21 has a cutting edge 22 directed in a direction almost parallel to the axial center line of the suction cup 12 and located at a very short distance outside the rim R of the suction cup. The enclosure 17 thus serves as a holder for the cutting blade 21-22.

In the position shown in FIG. 1, the pressure inside the pocket of the holder enclosure 17 is low and the cutting edge 22 of the blade 21 does not protrude into the surface wall 11.

In the position shown in FIG. 2, the pocket is pressurized, and deformingly expands and depresses downwardly along the adjacent outer wall of the suction cup, as shown, and the cutting tool 21-22 is moved downwards into the wall 11, inserted within a distance that is just a little greater than the thickness of this wall; that is to say, around 1mm in the case of a crystalline lens wall surface. As a result, this wall is incised along the complete run or curve of the cutting blade 21. It is therefore possible, in separating the apparatus from the lens wall 11, to remove the portion at the center of the incision which is held within and by the suction cup rim R during the maintaining of the suction.

The cutting tool can be moved by mechanical means. However, according to the most favored realization, the cutting tool is preferably supported by the lower rim or edge of the deformable, ring shaped holder enclosure 17, which is fixed around the suction cup and is connected to the source of pressure 19 that is capable of deforming the enclosure and thus pushing the cutting tool towards the eye after the suction cup is fixed on the eye.

The deformable enclosure 17 may be a ring-shaped cylinder in which a ring-shaped piston carrying the cutting tool can be moved. However, in the embodiment illustrated, the balloon-like enclosure holder was preferred to prevent any risk of jamming of pistons.

Further modifications will occur to those skilled in this art and such are considered to fall within the spirit and scope of the invention as defined in the appended claims.

What is claimed is:

1. A method of surgical incision along a closed curve, such as a circle, of a surface to be cut, so as to remove the portion thereof within said close curve, such as the inner circular disc portion of the crystalline lens of the eye, said method comprising, suction-attaching a cup to the said surface with said portion thereof lying within the opening of the cup and with the surface-attached cup rim defining said curve; disposing a cutting blade held a slight distance external to said cup rim by a holder positioned against the outer wall of the cup above the said cup rim; depressing the holder along said outer wall to insert the cutting blade into said surface; and moving the holder and cutting blade along the cup rim to incise the periphery of said portion of the surface within the said cup rim; and removing the cup and attached and incised surface portion as a unit, during the continued suction.

2. A method as claimed in claim 1 and in which the depressing step is effected by applying pressure to the holder to force the cutting blade into said surface.

3. A method as claimed in claim 2 and in which the depressing is effected by carrying the cutting blade along its lower edge along a deformable enclosure while responding to pressure introduced into the enclosure, deformably to move the cutting blade downward into the surface to incise the same.

4. A method as claimed in claim 3 and in which the suction is applied through the inner lumen of a concentric double-lumen needle communicating with the interior of the cup and the pressure is applied to said enclosure through the outer lumen of the needle.

5. Apparatus for performing an incision in the wall of the eye, characterized by the following elements: (a) a suction cup which can be fixed on the wall of the eye; (b) a cutting tool the cutting edge of which is in the shape of a closed curve, in particular a circle, which surrounds tightly the rim of the suction cup, and is capable of moving along the rim of the suction cup in order to penetrate into the wall of the eye, and to incise along the closed curve; (c) means to create suction in the central zone of the suction cup in order to attach it firmly on the wall of the eye; and (d) means to move the cutting tool along the rim of the suction cup to enable it to penetrate into the wall at a depth at least equal to the thickness of this wall, and in which the cutting tool is held by the wall of a deformable ring-shaped enclosure which surrounds the wall of the suction cup and is connected to a source of pressure capable of deforming the ring-shaped enclosure and thus pushing the cutting tool towards the eye when the suction cup is attached on the eye.

6. Apparatus according to claim 5 and in which the deformable ring-shaped enclosure is of balloon-like structure.

7. Apparatus according to claim 5 and in which the suction cup and the deformable ring-shaped enclosure are carried by a double-lumen needle, the center of the suction cup being connected to a source of suction through one of the lumens of the needle, and the interior of the deformable ring-shaped enclosure being connected to a source of pressure by the other lumen.

8. Apparatus for surgical incision along a closed curve of a surface such as the crystalline lens of the eye and the like to be cut so as to remove the portion thereof within said closed curve, having, in combination, an inverted suction cup provided with means for suction-attaching the rim thereof to said surface with said surface portion lying within the opening of the cup bounded by the closed curve of said rim; a cutting blade provided on holder means positioned adjacent the outer wall of the cup and maintaining the cutting blade a slight distance outside said rim; means for depressing the holder means to insert the cutting blade into said surface to enable incision along a closed curve outside said rim; and means for removing the said cup with the attached incised portion of said surface.

9. Apparatus as claimed in claim 8 and in which said cutting blade comprises a cutting ring concentrically around said rim.

10. Apparatus as claimed in claim 8 and in which said suction cup and holder are substantially concentrically conical.

11. Apparatus as claimed in claim 10 and in which means is provided for applying pressure to said holder means to cause the cutting blade to cut into said surface.

12. Apparatus as claimed in claim 11 and in which said holder means comprises a pressure-inflatable deformable envelope carrying the cutting blade at its lower edge adjacent but external to said suction cup rim.

13. Apparatus as claimed in claim 12 and in which double-lumen means is provided, one communicating with the inside of the suction cup to create suction therewithin, and the other communicating with pressure means.

* * * * *